United States Patent [19]

Glatz

[11] Patent Number: 5,167,827
[45] Date of Patent: Dec. 1, 1992

[54] CHROMATOGRAPHIC DETERMINATION OF IONS

[75] Inventor: Bernd Glatz, Leonberg, Fed. Rep. of Germany

[73] Assignee: Hewlett-Packard Company, Palo Alto, Calif.

[21] Appl. No.: 653,018

[22] Filed: Feb. 8, 1991

[30] Foreign Application Priority Data

Apr. 27, 1990 [EP] European Pat. Off. ......... 90108022.6

[51] Int. Cl.$^5$ ............................................. B01D 15/08
[52] U.S. Cl. ................................ 210/656; 210/198.2; 422/70; 436/161
[58] Field of Search ...................... 210/198.2, 656, 635; 73/61.1 C; 422/70; 436/161

[56] References Cited

U.S. PATENT DOCUMENTS

| | | | |
|---|---|---|---|
| 3,315,002 | 4/1967 | Small | 260/637 |
| 4,042,327 | 8/1977 | Haney et al. | 210/656 |
| 4,265,634 | 5/1981 | Pohl | 210/656 |
| 4,455,233 | 6/1984 | Pohl et al. | 210/656 |
| 4,925,567 | 5/1990 | McAleese | 210/656 |
| 4,927,539 | 5/1990 | Stevens et al. | 210/656 |

OTHER PUBLICATIONS

Frank G. P. Mullins, "Analyst", vol. 112, pp. 665-671 (1987).
B. E. Andrew, "LC-GC", vol. 4, No. 10, pp. 1026-1028 (1987).
E. Heftmann (editor), "Chromatography", vol. 22B, Elsevier Scientific Publishing Co., Amsterdam (1983), pp. B471-B472.
L. R. Snyder and J. J. Kirkland, "Introduction to Modern Liquid Chromatography", Wiley, New York (1979), pp. 292-295, 326-329, 452-483.
Wheals, Journal of Chromatography, vol. 402, pp. 115-126 (1987).
Cassidy and Elchuk, Dynamically Coated Columns for the Separation of Metal Ions and Anions by Ion Chromatography Anal. Chem. vol. 54, pp. 1558-1563 (1982).
Reeve, Journal of Chromatography, vol. 177, pp. 393-397 (1979).

*Primary Examiner*—Mary Lynn Theisen
*Assistant Examiner*—Sun Uk Kim

[57] ABSTRACT

Herein described is a process for the chromatographic determination of ions, particularly anions on a reversed-phase column, in which sample ions are introduced into a mobile phase containing a modifier and a counterion, the mobile phase with the modifier, counterion and sample ions is passed through the column and, after separation with the aid of a suitable detection method, preferably an indirect UV-detection method, the individual sample ions are determined quantitatively via the decrease the counterion concentration in the eluent. In this process the mobile phase is a mixture of water an an organic solvent and has a pH-value of more than 5. The modifier used is a quaternary ammonium hydroxide of formula $$\left[\begin{array}{c} R_1 \\ R_2-N^+-R_4 \\ R_3 \end{array}\right] OH^-$$

in which at least one radical is a straight-chained or branched alkyl radical with at least 8 and up to 20, more particularly 12 to 18 C-atoms. Prior to the passage of the mobile phase containing the sample ions, the reversed-phase column is preferably brought into equilibrium with the modifier, particularly with the modifier and the counterior. Trimethyl hexadecyl ammonium hydroxide is preferable used as the quaternary ammonium hydroxide. Also described herein is the use of said quaternary ammonium hydroxides for the quantitative chromatographic determination of ions and in particular for the determination of inorganic anions, as well as a reversed-phase material chromatographic column obtained through the conditioning with the modifier.

12 Claims, 7 Drawing Sheets

CHROMATOGRAPHIC DETERMINATION OF IONS

BACKGROUND OF THE INVENTION

The invention relates to a process for the chromatographic determination of ions, particularly anions on a reversed-phase column.

Ever since the arrival of ion chromatography there have been constant improvements to the quantitative analysis of organic and inorganic ions, particularly anions. Due to the poorer column or separation efficiency and the high price, as well as the instability of ion exchange columns, so-called reversed-phase columns have been investigated. In addition, the ions to be determined have been determined by indirect detection methods, such as e.g. indirect identification in the UV-spectral range. However, the chromatograms obtained with reversed-phase columns and indirect identification methods frequently have additional peaks (so-called system peaks) or poorly formed peaks, which make the detection and quantitative determination of the individual ions difficult or even impossible.

The publication by Frank G. P. Mullins (Analyst, May 1987, Vol. 112, pp. 665 to 671) describes an ion chromatographic process for the determination of inorganic anions by an indirect UV-detection method. The column used is dynamically loaded with hexadecyl trimethyl ammonium bromide. Although the chromatogram has no system peaks, not all inorganic anions can be determined, (as e.g. defined by DIN or EPA standards). Thus, it is not possible to detect fluoride and sulphate ions. In LC-GC, 1987, Vol. 4, No. 10, p. 1026 ff, B. E. Andrew describes the use of quaternary ammonium compounds for the ion chromatography of anions. Tetraalkyl ammonium hydroxides are used as ammonium compounds and the straight-chain alkyl radical can contain 1 to 5 C-atoms. In the ion chromatographic determination according to Andrew, system peaks occur in the chromatogram and it is not possible to analyze the anions in one chromatographic run. Andrew also pointed out that a variation in the chain length of the alkyl chains led to no advantages regarding the performance of the process.

SUMMARY OF THE INVENTION

The present invention provides an ion chromatographic column and process which permit a quantitative determination of ions with a high selectivity without disturbing system peaks or peak deformations in the chromatogram. In particular, the invention provides for the chromatographic determination of anions, and preferably inorganic anions, in which the anions can be simultaneously quantified in a single chromatographic run.

This invention is particularly pointed out in the appended claims. In general, the invention provides an ion chromatographic process in which sample ions are introduced into a mobile phase, which contains a modifier and a counterion, the mobile phase with modifier, counterion and sample ions is passed through the column and, following separation the anions are quantified with the aid of a suitable detection method, preferably an indirect detection method, the individual sample ions are quantitatively determined via the concentration decrease of the counterion in the eluent and in which the mobile phase is a mixture of water and an organic solvent and has a pH-value of more than 5 and as the modifier a quaternary ammonium hydroxide of formula below is used

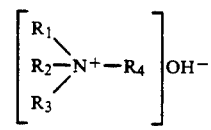

in which at least one R-radical is a straight-chain or branched alkyl radical with at least 8 and up to 20 and more, particularly 12 to 18 C-atoms. The remaining radicals are the same or different and have 1 to 20 C-atoms, particularly 1 to 10 C-atoms. Preferably the concentration of the ions to be quantitatively determined in the sample is no greater than 500 ppm.

DESCRIPTION OF THE INVENTION

Figure 1:
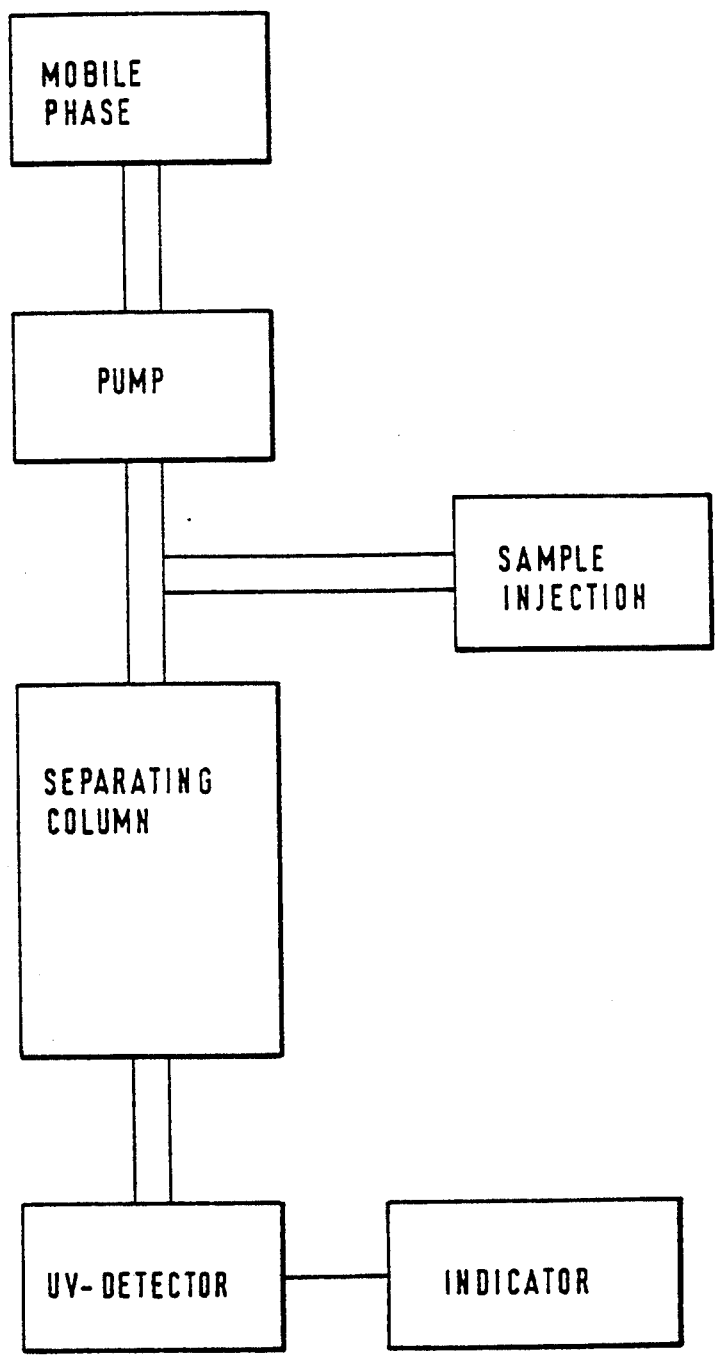
FIG. 1: a flow chart of an apparatus suitable for performing the inventive process.

Compared with known processes, the process according to the invention has the advantages that, by using an inexpensive, stable column and with low overall costs, it is possible to separate in a single chromatographic operation all the ions to be determined and in particular anions and can be quantitatively determined with high sensitivity, without disturbing peaks or peak deformations occurring. Thus, it is possible to establish the presence of and the quantity of fluoride, chloride, bromide, nitrite, nitrate, phosphate and sulphate ions in a single operation, i.e. a single chromatographic run. According to the invention, standard columns and standard HPLC equipment can be used, so that chromatographic determination is possible in a short time with easy handling. Due to the fact that the modifier is used in the hydroxide form, apart from the counterions, no further impurity ions are present, which could disturb the detection of the sample ions.

The invention can be carried out using known reversed-phase columns, particularly those conventionally having carbon chains with 8 to below 20 C-atoms, and in particular reversed-phase columns with $C_8$, $C_{12}$ and $C_{18}$-chains which are commercially available. In particular, reversed-phase columns with a $C_{18}$-chain can be used in the invention. The number of carbon atoms of the reversed-phase column need not coincide with the number of carbon atoms of the modifier, i.e. the alkyl radical of the packing material of the column need not be the same as the alkyl radical of the modifier. According to the invention other standard reversed-phase column types can be used. These can be columns based on polyacrylamide, which have a $C_{18}$-chain, or a column based on carbon, whose behavior largely corresponds to a conventional reversed-phase column. Preference is given to the use of columns based on silica. It is possible to use spherical material with a diameter of e.g. 5 μm, but also irregular material.

The length of the column used in the inventive process is more than 2 cm and is normally less than 20 cm, preference being given to a range of 10 to 15 cm. A length below 2 cm is not advantageous, because with such small column length no complete separation of the ions to be determined is possible. A preferred column length is e.g. 12.5 cm.

The flow rate of the mobile phase through the column is not critical. In the case of a 4 mm column diameter, the flow rate is e.g. 0.2 to 5 ml/min, a range of 1 to 3 ml/min being preferred. The detection limit of the inventive process without enrichment is in the lower ppb (parts per billion) range, so that the process is also suitable for the highest demands.

In the case of the inventive process, the mobile phase is preferably allowed to be recycled Thus, the column can be brought into equilibrium, stable conditions are created and solvent consumption is reduced.

A preferred embodiment of the invention occurs if a quaternary ammonium hydroxide is used, in which the $R_1$, $R_2$ and $R_3$ radicals are the same or different and have 1 to 10 C-atoms and the $R_4$ radical has between 8 and up to 20, and in particular 12 to 18 C-atoms. Preferably the $R_1$, $R_2$ and $R_3$ radicals are the same and have 1 to 5 C-atoms and the $R_4$ radical has a straight-chain form and has between 14 and 18, in particular 16 C-atoms. The process performed using said quaternary ammonium hydroxides leads to chromatograms, which permit a particularly good quantitative determination of anions in a single chromatographic run. Particular preference is given to the use in this invention of trimethyl hexadecyl ammonium hydroxide as the quaternary ammonium hydroxide.

The quantity of quaternary ammonium hydroxide modifier contained in the mobile phase can be varied within a wide range and is only dependent on a favorable performance of the process. Preferably the modifier is contained in the mobile phase in a concentration of about 0.05 to 1.5 molar.

An indirect detection method can be used for the detection of the sample ions and the latter can be quantitatively determined via the decrease of the counterion concentration in the eluent. Conductivity, indirect fluorescence and electrochemical measurements are also possible and for the two former methods the increase in the conductivity or the decrease in the fluorescence of the counterion is determined, while in the latter method oxidizable or reducible sample ions are measured. It is also possible, in a modification of the inventive process, to e.g. quantitatively determine anions with the aid of a direct UV-method revealing an absorption in the ultraviolet range of the spectrum. This is preferably the nitrate and nitrite ion. It is particularly advantageous if the indirect detection method is constituted by an indirect determination of the sample ions in the ultraviolet range of the spectrum.

For indirect detection purposes, it is possible to use all counterions which have a detectable physicochemical property and via whose concentration decrease in the eluent the sample ions can be quantitatively determined. Preferably the counterion is the anion of organic acids or sulphonic acids. Such anions are e.g. the anions of a benzene sulphonic, salicylic and in particular phthalic acid. Due to its absorption in the ultraviolet range of the spectrum, the phthalate ion is particularly suitable for performing the inventive process, in conjunction with the indirect determination of the sample ions in the UV-spectral range. The counterion concentration in the mobile phase can be varied over a wide range. A too high concentration increase leads to a sensitivity loss and to a poorer separation of the individual ions. If the concentration is excessively reduced, the column capacity may be low. A preferred concentration range for the counterion in the mobile phase is between about $6 \times 10^{-3}$ to $1 \times 10^{-4}$ and in particular about $6 \times 10^{-3}$ to $4 \times 10^{-4}$ molar.

The mobile phase containing the quaternary ammonium hydroxide modifier and the counterion comprises a mixture of water and an organic solvent. It is possible to use various organic solvents, such as e.g. acetonitrile, methanol, dimethyl formamide and dimethyl sulphoxide. The use of less polar organic solvents is possible, the first-mentioned polar, organic solvents and more especially acetonitrile being preferred. Particularly good results are obtained when using a mobile phase comprising a mixture of about 65 to 95 vol % (and in particular approximately 80 vol %) of water and about 5 to 35 vol % (and in particular approximately 20 vol %) of organic solvent.

In the process according to the invention, the mobile phase has a pH-value of more than 5. pH-values between 6 and 12 and more especially between about 7 and 9 are preferred. If the pH-value is in the alkaline range, it can be adjusted with the aid of a base, particularly sodium hydroxide solution. Through the choice of the pH-value, it is possible to control the inventive process in such a way that under all circumstances the simultaneous detection of all the ions to be determined in a single chromatographic operation is possible.

The process according to the invention can be performed at elevated temperature, at ambient temperature and also at lower than ambient temperatures. Preferably the temperature is between about 0° and 80° C., particularly between about 20° and 50° C. Thermostatic control can e.g. take place at higher than ambient temperatures by placing the column in a thermostatically controlled area (oven). It is advantageous if the chosen temperature is kept substantially constant during the process, preferably with a variation of max. ±1° C. This temperature constancy may be necessary if the chromatogram has a different appearance at different temperatures. Thus, it is possible that the time intervals with which the anions are eluted by the column will vary with the temperature, or for there even to be a peak sequence reversal. This phenomenon can be attributed to the temperature dependence of the phase equilibria between the stationary and mobile phase. Preferably the temperature is kept constant with a variation of max. ±0.5° C. and in particular ±0.2° C. If e.g. the precision with regards to the reproducibility of the times at which the individual ions are eluted by the column is to be better than 1%, then the set temperature kept constant with a temperature fluctuation of max.±0.5° C. If several chromatographic operations are performed successively, the temperature at which the process is performed is not only kept constant during the individual analyses, but also between said analyses, so that reproducible and comparable results are obtained. The embodiments of the inventive process, in which the temperature is kept constant, are particularly suitable for use in an automated and in particular a computer-controlled operation, evaluated with the aid of a computer.

The hydraulic pressure under which the mobile phase is passed through the column is dependent on the packing material and can be varied within wide limits. If spherical packing materials are used as the column material, a hydraulic pressure of 50 to 200 bar is preferred at a particle diameter of e.g. 5 μm. If smaller diameter particles, e.g. 3 μm are used, it can be appropriate to use a higher pressure, the pressure rising quadratically with decreasing particle diameter.

The invention also relates to the use of a quaternary ammonium hydroxide of formula

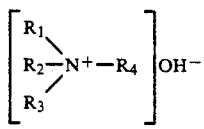

for the quantitative chromatographic determination of ions, in which at least one of the R-substituents is a straight-chain or branched alkyl radical with at least 8 and up to 20, more particularly 12 to 18 C-atoms and the remaining radicals are the same or different and have 1 to 20 and in particular 1 to 10 C-atoms. It is advantageous if a quaternary ammonium hydroxide is used, in which the $R_1$, $R_2$ and $R_3$ radicals are the same and have 1 to 5 C-atoms and in which the $R_4$ radical has a straight-chain form and has between 4 and 18, particularly 16 C-atoms. Once again the use of trimethyl hexadecyl ammonium hydroxide is preferred among these quaternary ammonium hydroxides.

The inventive use inter alia relates to the quantitative determination of ions, particularly anions, in water, such as e.g. in waste or drinking water, in food stuffs, such as e.g. beer, wine, juices or vegetables, as well as in biotechnological and physiological substances, such as blood and urine, or in liquids used in the electrical more particularly to the use of quaternary ammonium hydroxides for determining inorganic ions in a single chromatographic operation and preferably at least fluoride, chloride, bromide, nitrite, nitrate, phosphate and sulphate are simultaneously quantified.

Finally, the invention relates to a chromatographic column, particularly suitable for performing the inventive process, in which the column contains a reversed-phase material, which is conditioned with a modifier, more particularly a modifier and a counterion and the modifier is a quaternary ammonium hydroxide of formula

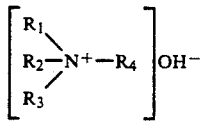

in which at least one of the R-substituents is a straight-chain or branched alkyl radical with at least 8 and up to 20, more particularly 12 to 18 C-atoms and the remaining radical are the same or different and have 1 to 20, particularly 1 to 10 C-atoms. The reversed-phase material of the chromatographic column is preferably conditioned with a modifier, whose $R_1$, $R_2$ and $R_3$ radicals are the same and have 1 to 4 C-atoms and whose $R_4$ radical has a straight-chain form and has between 14 and 18 and in particular 16 C-atoms. Preferably the quaternary ammonium hydroxide is used for conditioning purposes is trimethyl hexadecyl ammonium hydroxide. The inventive column leads to a very good separation of all ions and in particular anions to be determined in a single operation and with high sensitivity. The column can be obtained at low costs and the column selectivity is maintained even after a large number of determinations, such as e.g. after more than 1000 injections.

The following examples and drawings serve to illustrate the invention. In the examples and drawings the individual features can be realized either singly, or in the form of random combinations.

FIG. 1 is the flow chart of an apparatus for performing an embodiment of the process according to the invention. By means of a pump, the mobile phase is pumped through the chromatographic column and the counterions contained in the mobile phase are visible by a UV-detector. There is also a sample injection enabling the sample ions to be introduced into the mobile phase. The inventive process is normally performed as follows. A mobile phase of a mixture of water and an organic solvent is prepared, which contains a modifier and a counterion in a concentration of 0.05 to 1.5 molar or $6 \times 10^{-3}$ to $1 \times 10^{-4}$ molar and which has a pH-value of more than 5. This mobile phase is pumped through the chromatographic column using a liquid pressure pump at a pressure of about 50 to 200 bar, the column being kept at a temperature between 20° and 80° C. with a variation of max. ±1° C. approximately 2 to 4 hours an equilibrium has established between the stationary and mobile phase. By means of sample injection, the sample ions to be determined are then applied to the chromatographic column and are successively eluted by the latter, accompanied by a further continuous passage of the mobile phase. The individual ions are quantitatively determined via the concentration decrease of the counterion in the eluent.

EXAMPLE 1

A 200 mm long and diameter 4.6 mm chromatographic column is filled with Hypersil ODS, of 5 μm spherical particles. This column is conditioned with a mobile phase of 73% water and 27% acetonitrile, which contains 0.8 mmole of a hexadecyl trimethyl ammonium ion and 2 mmole of phthalic acid and is set to a pH-value of 7.2 with a sodium hydroxide solution. The mobile phase flow rate is 2 ml/min. The phthalate counterion is detected at 254 nm. After the equilibrium has been established between the stationary and mobile phase a sample solution, which contains the nitrate ions, is introduced into the mobile phase and the elution of the nitrate ions by the column is observed.

Figure 2A:
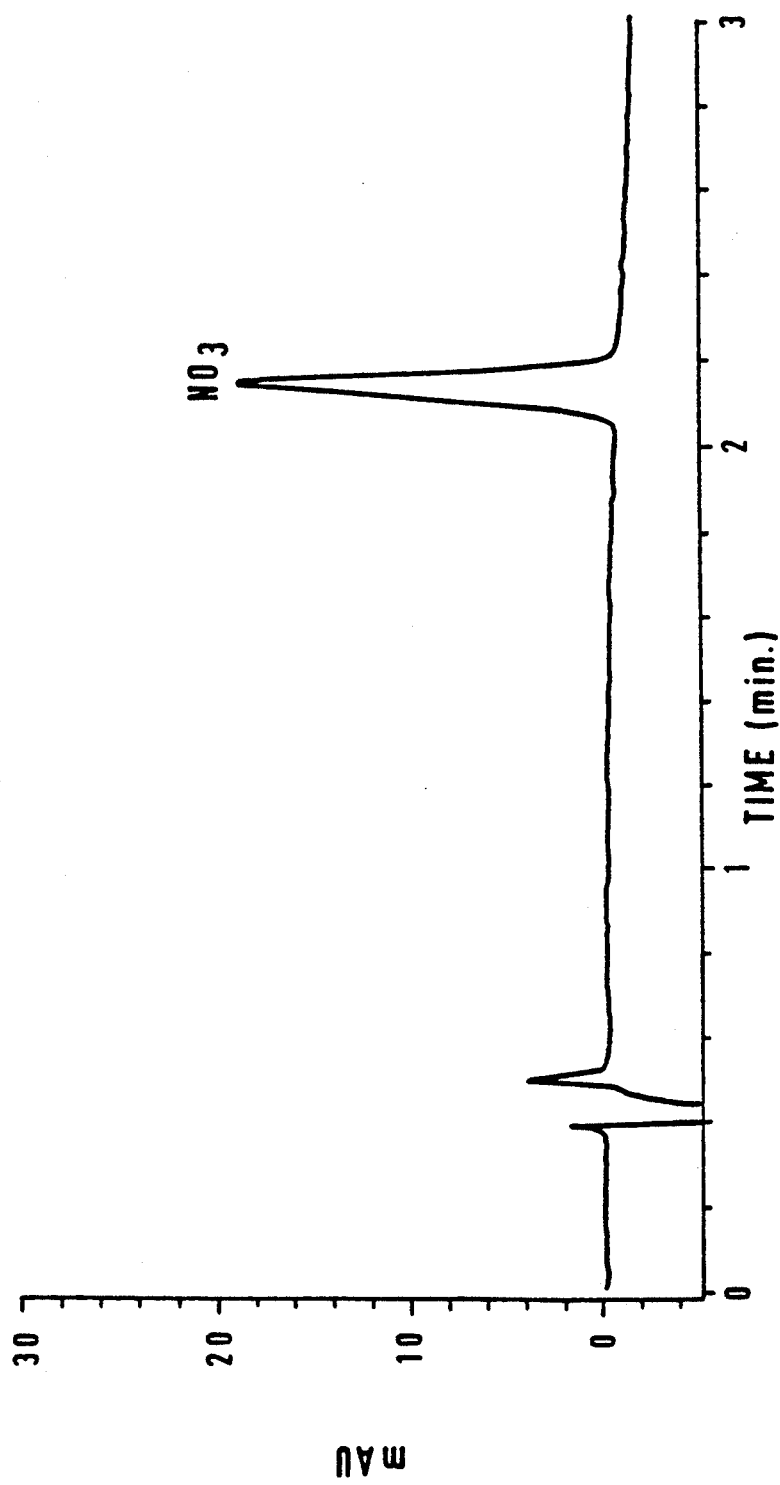
FIG. 2a: the detection of the nitrate ion according to an embodiment of the inventive process.

FIG. 2a shows the chromatogram when using hexadecyl trimethyl ammonium hydroxide as the modifier Roughly 2 minutes after the application of the sample solution, a symmetrical peak appears from which the content of nitrate ions can be quantitatively determined.

Figure 2B:
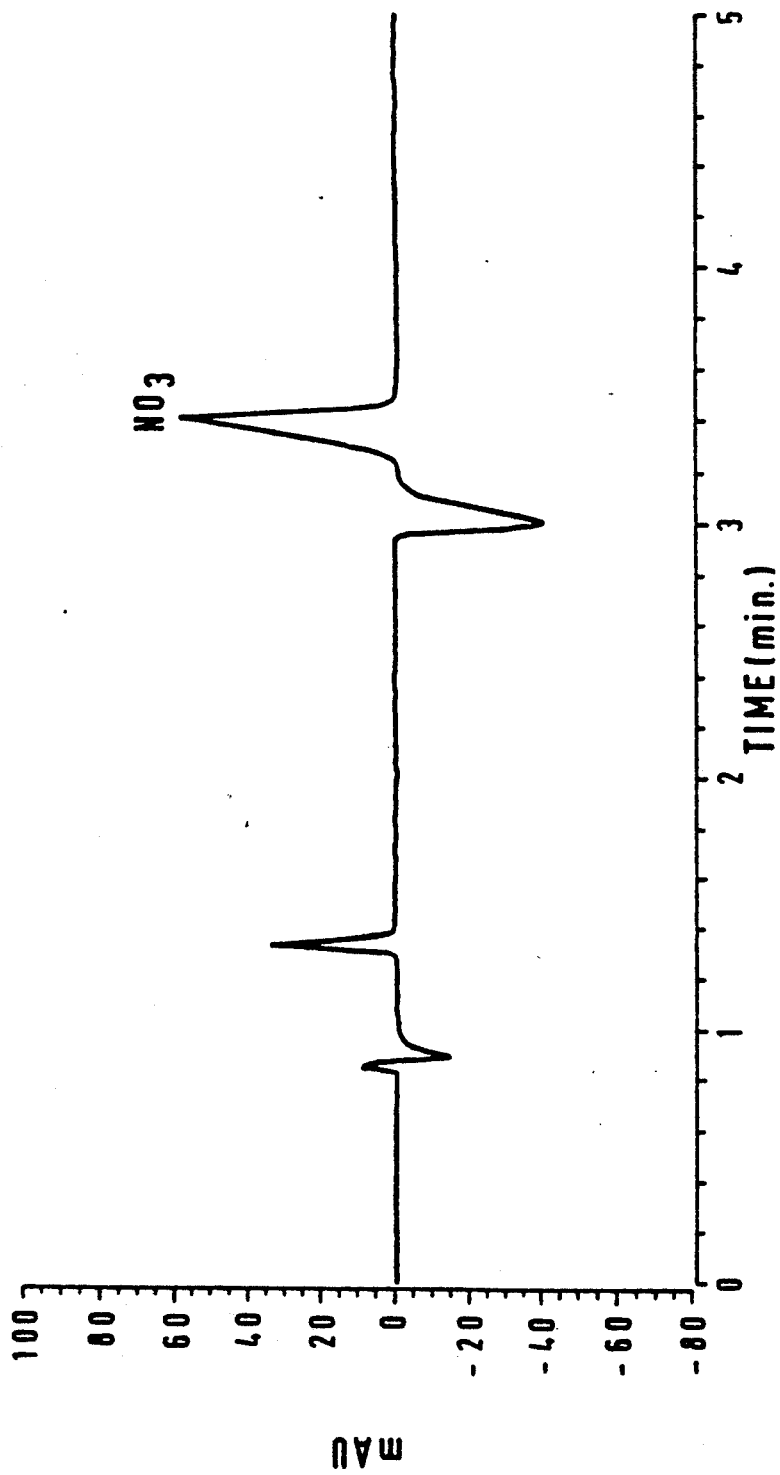
FIG. 2b: the detection of the nitrate ion according to a prior art comparison process.

FIG. 2b shows the chromatogram when hexadecyl trimethyl ammonium bromide is used as the modifier. After roughly 3 minutes a disturbing system peak appears, which does not occur when performing the inventive process.

EXAMPLE 2

Figure 3:
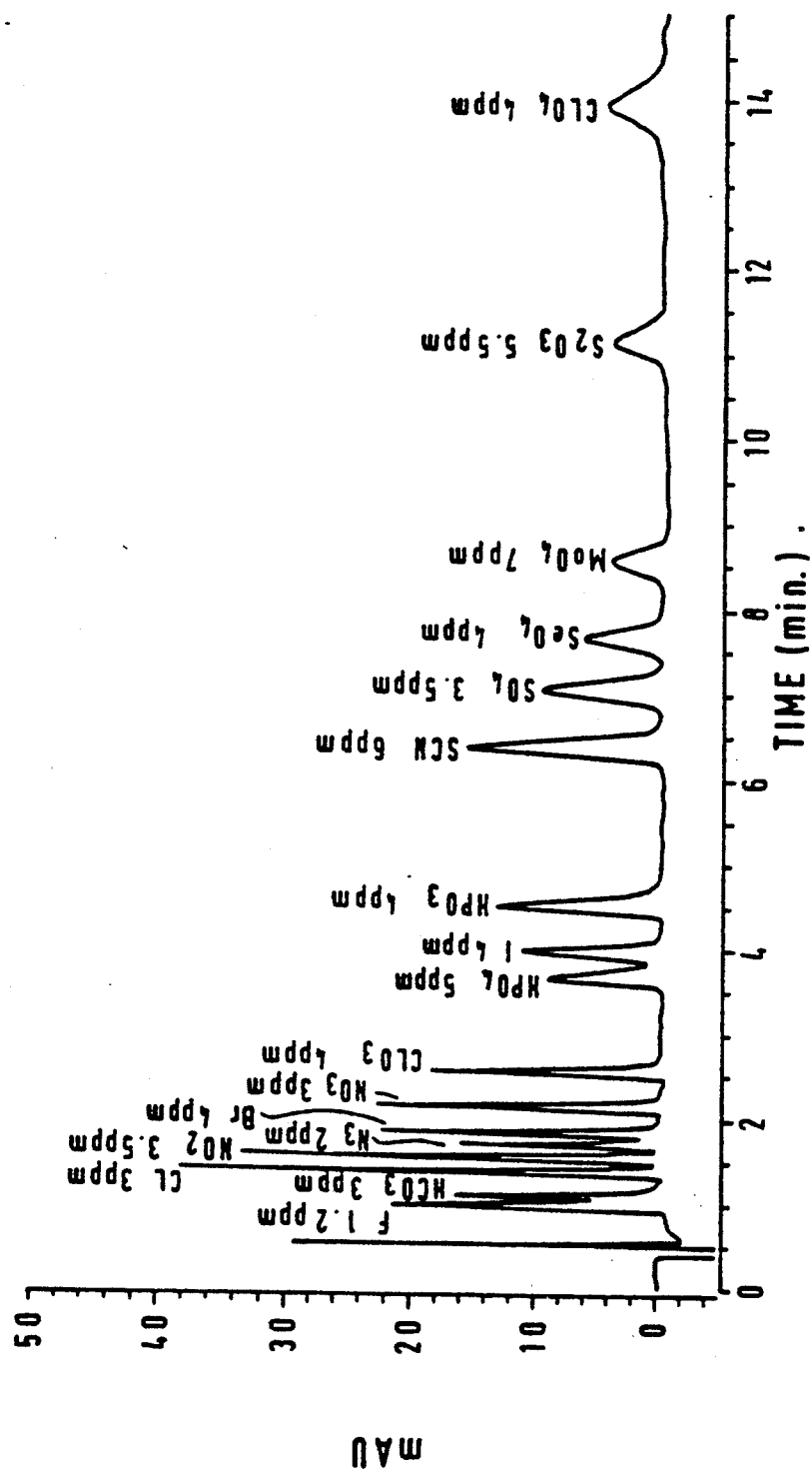
FIG. 3: the detection of 17 anions according to an embodiment of the inventive process.

The column described in Example 1 is conditioned with the mobile phase containing hexadecyl trimethyl ammonium hydroxide as the modifier. The other conditions are as in Example 1. After establishing the equilibrium, a sample solution containing 17 anions is introduced into the mobile phase. The chromatogram shown in FIG. 3 is obtained within 15 minutes. Thus, in a single chromatographic operation all 17 anions are separated from one another and can be quantitatively determined.

EXAMPLE 3

A 100 mm long, diameter 4.6 mm column is filled with Hypersil ODS. This column is then conditioned with a mobile phase of 82% water and 18% acetonitrile for 3 hours for obtaining an equilibrium. The mobile phase contained 0.8 mmole of hexadecyl trimethyl ammonium hydroxide and 2 mmole of phthalic acid and is set to a pH-value of 8.4 with a sodium hydroxide solution. The flow rate of the mobile phase is 2 ml/min. The phthalic counterions are detected at a wavelength of 266 nm. In three different tests, the chromatographic column is thermostated to 3 different temperatures, namely 19° C., 30° C. and 40° C., the temperature being kept constant with an accuracy of ±0.5° C. or less. After setting the equilibrium, 50 µl of sample solution containing 8 different anions are injected. These anions are eluted by the column through the mobile phase and determined with the aid of the indirect UV-method.

Figure 4:
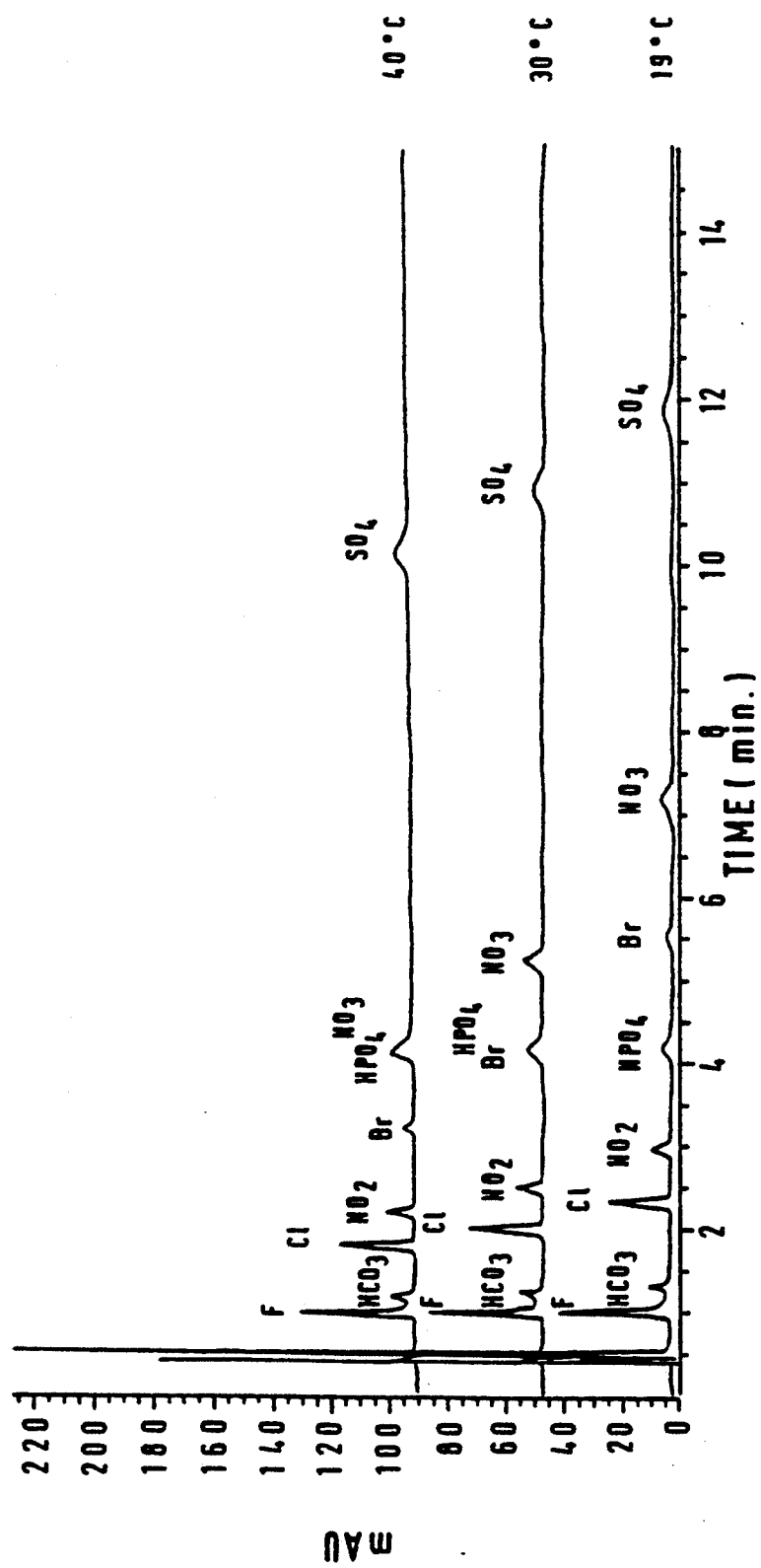
FIG. 4: the temperature dependence of the chromatogram.

FIG. 4 shows the results of 3 chromatographic determinations at the 3 different temperatures. At 19° C. there is a complete separation of all the anions, so that a separate quantitative determination of the anions is possible. At 30° C. the bromide and phosphate ions are not completely separated from one another, but the other six anions can be quantified. At 40° C. the nitrate and phosphate ions are not completely separated from one another, but the other six anions can be quantified.

FIG. 4 shows that through the choice of suitable conditions and in particular the temperature setting, it is possible to achieve a simultaneous determination of all the anions in a single chromatographic step.

EXAMPLE 4

A 125 mm long, diameter 4.0 mm chromatographic column is filled with Lichrospher 100 RP-18 and is conditioned with a mobile phase of 82% water and 18% acetonitrile, which contains 0.8 mmole of hexadecyl trimethyl ammonium hydroxide and 2 mmole of phthalic acid and is adjusted to a pH-value of 8.6 with a sodium hydroxide solution. The flow rate is 2.0 ml/min. Conditioning takes place for approximately 2 to 4 hours and is performed in three different passages at 38° C., 40° C. and 46° C. The temperature is kept constant with an accuracy of ±1° C. by a suitable thermostat (oven). After setting the equilibrium, 50 µl of a sample solution containing 8 different anions is introduced into the mobile phase. The counterions are detected at a wavelength of 266 nm.

Figure 5:
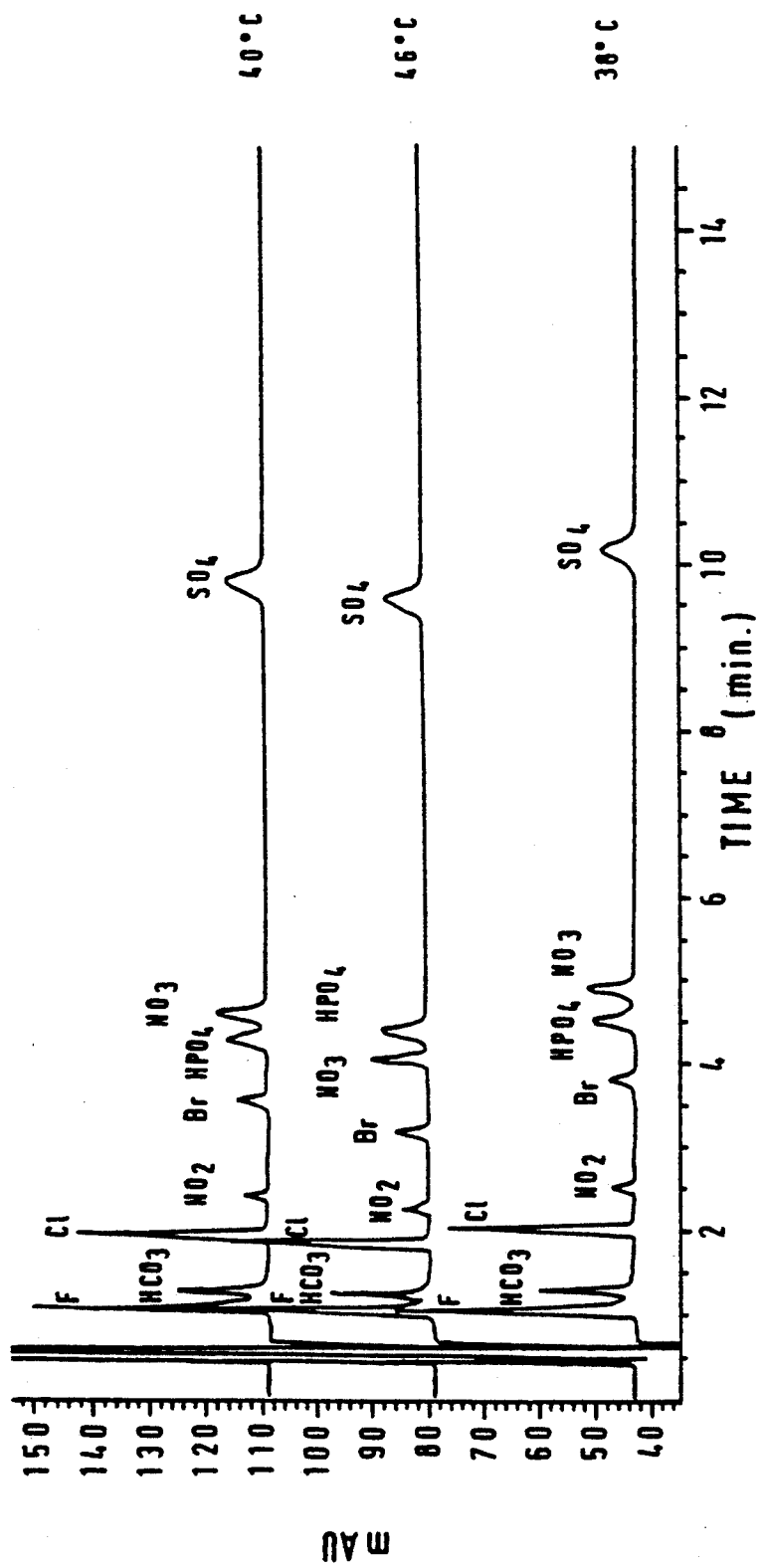
FIG. 5: the temperature dependence of the chromatogram according to another embodiment of the inventive process.

FIG. 5 shows the results of the determinations performed at said 3 temperatures. It can be seen that all 3 temperatures there is a complete separation of the individual anions and a quantitative determination of the individual ions is possible.

EXAMPLE 5

Figure 6:
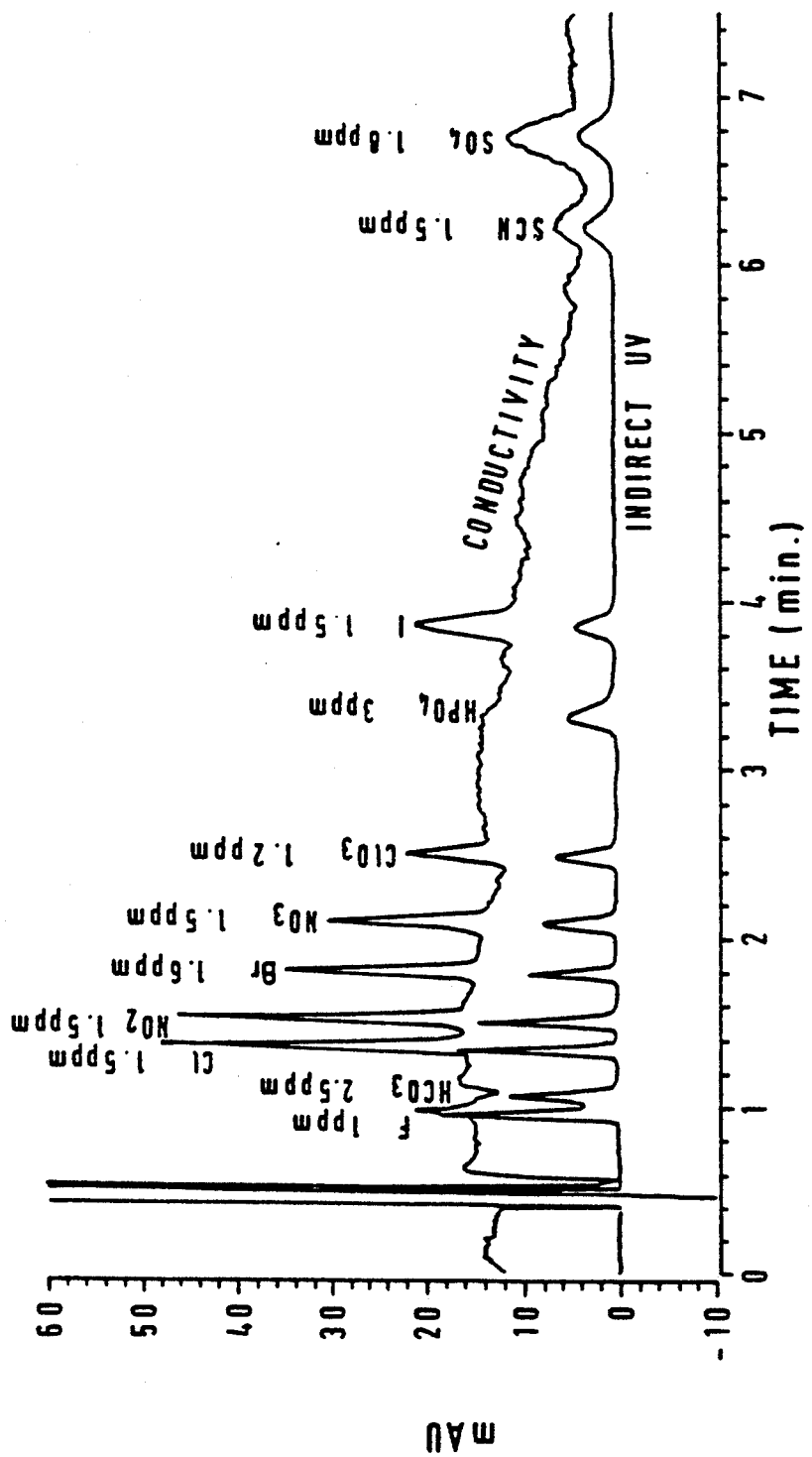
FIG. 6: the comparison of the chromatograms of embodiments of the inventive process, in which the ions are detected with the aid of the indirect UV-method and with the aid of the conductivity method.

A column filled with Hypersil ODS according to Example 2 is conditioned as in the latter. A sample solution containing 11 different anions is then introduced into the mobile phase. The individual ions are eluted by the column and detected once with the indirect UV-method and on a further occasion with the conductivity method. The results of these two determinations are given in FIG. 6. The latter shows that both with the conductivity method and with the indirect UV-method, a determination of the anions contained in the sample solution is possible in one chromatographic run.

I claim:

1. A process for the chromatographic determination of ions without disturbing system peaks or peak deformations in the chromatogram in a reversed-phase chromatographic column which process comprises introducing sample ions into a mobile phase containing a modifier and a counterion, passing the mobile phase with the modifier, counterion and sample ions through said column, separating said sample ions and detecting the quantitatively determining the individual sample ions with the aid of an indirect ultraviolet detection method via the decrease in the concentration of the counterion in the eluent, in which process the mobile phase is a mixture of water and an organic solvent having a pH-value of between about 7 and 9, and the modifier is a quaternary ammonium hydroxide of formula

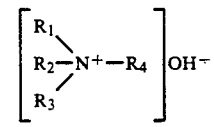

in which the $R_1$, $R_2$, $R_3$ and $R_4$ radicals are alkyl chains, which are the same or different and have 1 to 20 C-atoms and in which at least one radical is a straight-chain or branched alkyl radical with at least 8 and up to 20 C-atoms.

wherein the mobile phase contains about 5-35 volume percent polar organic solvent in water, wherein said modifier is present in the mobile phase in a concentration from about $0.05 \times 10^{-3}$ to $1.5 \times 10^{-3}$ molar, and said counterion is the anion of phthalic acid present in the mobile phase in a concentration from about $6 \times 10^{-3}$ to $1 \times 10^{-4}$ molar.

2. Process according to claim 1, wherein said column is a reversed-phase column and prior to said step of passing through of the mobile phase containing the sample ions, the column is brought into equilibrium with the modifier and the counterion.

3. Process according to claim 2 wherein said column is brought into equilibrium with a mobile phase which, apart from the sample ion content, has the same composition as the mobile phase used for determining the sample ions.

4. Process according to claim 1 wherein $R_1$, $R_2$ and $R_3$ are the same or different and have 1 to 10 C-atoms and $R_4$ has between 12 and 18 C-atoms.

5. Process according to claim 4 wherein $R_1$, $R_2$ and $R_3$ are the same and have 1 to 5 C-atoms and $R^4$ has a straight-chain form and has between 14 and 18 C-atoms.

6. Process according to claim 1 wherein trimethyl hexadecyl ammonium hydroxide is the quaternary ammonium hydroxide.

7. Process according to claim 1 wherein the counterion is contained in the mobile phase in a concentration of about $6\times 10^{-3}$ to $4\times 10^{-4}$ molar.

8. Process according to claim 1 wherein said process is performed at a temperature between about 0° and 80° C.

9. Process according to claim 1 wherein the temperature is kept constant during the process, with a maximum variation of ±0.5° C.

10. A process for the chromatographic determination of anions without disturbing system peaks or peak deformations in the chromatogram in a reversed-phase chromatographic column, which process comprises: conditioning said column to equilibrium with a mobile phase containing a modifier and a counterion with mobile phase contains about 5–35 vol. % polar organic solvent in water, introducing sample ions into said mobile phase and passing said mobile phase through said column, and separating said sample ions and detecting and quantitatively determining with the aid of an indirect ultraviolet detection method the individual sample ions via the decrease in the concentration of the counterion in the eluent, in which process the mobile phase has a pH between about 7 and 9, and the modifier is a quaternary ammonium hydroxide of the formula

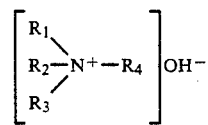

wherein $R_1$, $R_2$ and $R_3$ are alkyl radicals having from 1 to 5 c-atoms and $R_4$ is a straight chain alkyl radical having from about 14 to 18 C-atoms, said modifier being present in the mobile phase in a concentration from about $0.05\times 10^{-3}$ to $1.5\times 10^{-3}$ molar, and said counterion being a phthalate ion present in said mobile phase in a concentration from about $6\times 10^{-3}$ to $4\times 10^{-4}$ molar.

11. Process according to claim 10 wherein the quaternary ammonium hydroxide is trimethyl hexadecyl ammonium hydroxide.

12. Process according to claim 10 wherein said determination of ions is for determining fluoride, chloride, bromide, nitrite, nitrate, phosphate and sulphate in a single chromatographic run.

* * * * *

UNITED STATES PATENT AND TRADEMARK OFFICE
CERTIFICATE OF CORRECTION

PATENT NO. : 5,167,827
DATED : December 1, 1992
INVENTOR(S) : Glatz

It is certified that error appears in the above-identified patent and that said Letters Patent is hereby corrected as shown below:

In column 5, line 41, after "electrical" insert --industry such as e.g., plating baths. The invention relates--.

In column 6, line 27, delete "concentration" and substitute --concentrate--.

In column 6, line 27, delete "molar" and substitute --mmole--.

In column 6, line 28, delete "molar" and substitute --mmole--.

In column 6, line 33, after "C." insert --by means of a suitable thermo-stating device. After--.

Signed and Sealed this

Twenty-eight Day of March, 1995

Attest:

BRUCE LEHMAN

Attesting Officer      Commissioner of Patents and Trademarks